United States Patent
Timm et al.

(10) Patent No.: US 11,211,237 B2
(45) Date of Patent: Dec. 28, 2021

(54) MASS SPECTROMETRIC METHOD FOR DETERMINING THE PRESENCE OR ABSENCE OF A CHEMICAL ELEMENT IN AN ANALYTE

(71) Applicant: Bruker Daltonik GmbH, Bremen (DE)

(72) Inventors: Wiebke Andrea Timm, Grasberg (DE); Sebastian Wehner, Bremen (DE); Nikolas Kessler, Bremen (DE)

(*) Notice: Subject to any disclaimer, the term of this patent is extended or adjusted under 35 U.S.C. 154(b) by 171 days.

(21) Appl. No.: 16/774,571

(22) Filed: Jan. 28, 2020

(65) Prior Publication Data
US 2020/0243315 A1 Jul. 30, 2020

Related U.S. Application Data

(60) Provisional application No. 62/798,531, filed on Jan. 30, 2019.

(51) Int. Cl.
| | | |
|---|---|---|
| *H01J 49/00* | (2006.01) | |
| *G16C 20/20* | (2019.01) | |
| *G06K 9/00* | (2006.01) | |
| *G01N 30/72* | (2006.01) | |
| *H01J 49/04* | (2006.01) | |

(52) U.S. Cl.
CPC ...... *H01J 49/0095* (2013.01); *G06K 9/00496* (2013.01); *G16C 20/20* (2019.02); *H01J 49/0036* (2013.01); *G01N 30/7233* (2013.01); *H01J 49/0431* (2013.01)

(58) Field of Classification Search
CPC .... H01J 49/00; H01J 49/0095; H01J 49/0036; H01J 49/0431; H01J 49/0027; H01J 49/26; G06K 9/00496; G16C 20/20; G16C 20/10; G16C 20/70; G01N 30/7233
See application file for complete search history.

(56) References Cited

U.S. PATENT DOCUMENTS

| | | | |
|---|---|---|---|
| 7,781,729 B2 * | 8/2010 | Wang | G16C 20/20 250/282 |
| 9,111,735 B1 | 8/2015 | Nikolaev et al. | |
| 2008/0001079 A1 * | 1/2008 | Wang | H01J 49/0036 250/282 |

FOREIGN PATENT DOCUMENTS

| | | | | |
|---|---|---|---|---|
| EP | 2594936 A2 * | 5/2013 | | G01N 30/8675 |
| EP | 2128791 A2 | 8/2018 | | |
| GB | 2514836 A | 4/2020 | | |
| JP | 2009-539068 A * | 11/2009 | | H01J 49/0036 |

(Continued)

OTHER PUBLICATIONS

Bernhard Y Renard in NITPICK: peak identification for mass spectrometry data, BMC Bioinformatics 2008, 16 pages (Year: 2008).*

(Continued)

*Primary Examiner* — Tung S Lau
(74) *Attorney, Agent, or Firm* — Benoit & Côté Inc.

(57) ABSTRACT

The present invention relates to a mass spectrometric method for determining (predicting) the presence or absence of a chemical element in an analyte which provides valuable information towards reduction of complexity for annotating a chemical formula to the analyte. The method is based on representing a measured isotopic pattern of an analyte as a feature vector and assigning the feature vector to the presence/absence class using a machine learning algorithm, like a support vector machine (SVM) or an artificial neural network (NN).

20 Claims, 10 Drawing Sheets

(56) References Cited

FOREIGN PATENT DOCUMENTS

| JP | 6020315 B2 | * | 11/2016 | ............. G01N 27/62 |
|---|---|---|---|---|
| KR | 2008-0009326 A | * | 1/2008 | .......... H01J 49/0036 |
| KR | 10-0942815 B1 | * | 2/2010 | .......... H01J 49/0036 |
| WO | WO 2004/111609 A2 | * | 12/2004 | ............... G01N 1/00 |
| WO | 2005009039 A2 | | 1/2005 | |
| WO | WO 2005/040985 A | * | 5/2005 | ......... G06K 9/00496 |
| WO | WO 2019/094507 A1 | * | 5/2019 | ......... G01N 33/6848 |

OTHER PUBLICATIONS

Datta, S. et al. "Feature selection and machine learning with mass spectrometry data for distinguishing cancer and non-cancer samples", Statistical Methodology, vol. 3, p. 79-92, 2006.

Kind, T. et al. "Seven Golden Rules for heuristic filtering of molecular formulas obtained by accurate mass spectrometry", BMC Bioinformatics, vol. 8, 2007.

Zhang X. et al. "Recursive SVM feature selection and sample classification for mass-spectrometry and microarray data" BMC Bioinformatics, vol. 7, 2006.

* cited by examiner

| Element | Train Acc | Validation Acc | Sensitivity | Specificity |
|---|---|---|---|---|
| Na | 0.79 | 0.80 | 0.81 | 0.80 |
| K | 0.90 | 0.89 | 0.89 | 0.90 |
| P | 0.99 | 0.94 | 0.91 | 0.97 |
| S | 0.92 | 0.93 | 0.92 | 0.94 |
| F | 0.98 | 0.98 | 0.99 | 0.98 |
| Cl | 0.99 | 0.98 | 0.98 | 0.98 |
| Br | 0.99 | 0.99 | 0.99 | 1.00 |
| I | 0.98 | 1.00 | 1.00 | 1.00 |

| Element | Train Acc | Validation Acc | Sensitivity | Specificity |
|---------|-----------|----------------|-------------|-------------|
| Na | 0.89 | 0.91 | 0.92 | 0.89 |
| K | 0.97 | 0.96 | 0.96 | 0.96 |
| P | 0.93 | 0.93 | 0.91 | 0.94 |
| S | 0.94 | 0.97 | 0.98 | 0.97 |
| F | 0.93 | 0.93 | 0.96 | 0.91 |
| Cl | 0.98 | 0.98 | 0.97 | 0.99 |
| Br | 0.98 | 0.98 | 0.96 | 1.00 |
| I | 0.96 | 1.00 | 1.00 | 1.00 |

| Element | Train Acc | Validation Acc | Sensitivity | Specificity |
|---|---|---|---|---|
| Na | 0.89 | 0.89 | 0.92 | 0.87 |
| K | 0.96 | 0.97 | 0.97 | 0.97 |
| P | 0.93 | 0.93 | 0.91 | 0.94 |
| S | 0.94 | 0.97 | 0.96 | 0.97 |
| F | 0.93 | 0.93 | 0.96 | 0.90 |
| Cl | 0.98 | 0.98 | 0.97 | 0.99 |
| Br | 0.98 | 0.98 | 0.96 | 1.00 |
| I | 0.97 | 1.00 | 1.00 | 1.00 |

| Element | Train Acc | Validation Acc | Sensitivity | Specificity |
|---------|-----------|----------------|-------------|-------------|
| Na | 0.79 | 0.80 | 0.81 | 0.80 |
| K | 0.90 | 0.89 | 0.89 | 0.90 |
| P | 0.99 | 0.94 | 0.91 | 0.97 |
| S | 0.92 | 0.93 | 0.92 | 0.94 |
| F | 0.98 | 0.98 | 0.99 | 0.98 |
| Cl | 0.99 | 0.98 | 0.98 | 0.98 |
| Br | 0.99 | 0.99 | 0.99 | 1.00 |
| I | 0.98 | 1.00 | 1.00 | 1.00 |

| Element | Train Acc | Validation Acc | Sensitivity | Specificity |
|---------|-----------|----------------|-------------|-------------|
| Na | 0.89 | 0.91 | 0.92 | 0.89 |
| K | 0.97 | 0.96 | 0.96 | 0.96 |
| P | 0.93 | 0.93 | 0.91 | 0.94 |
| S | 0.94 | 0.97 | 0.96 | 0.97 |
| F | 0.93 | 0.93 | 0.96 | 0.91 |
| Cl | 0.98 | 0.98 | 0.97 | 0.99 |
| Br | 0.98 | 0.98 | 0.96 | 1.00 |
| I | 0.96 | 1.00 | 1.00 | 1.00 |

| Element | Train Acc | Validation Acc | Sensitivity | Specificity |
|---------|-----------|----------------|-------------|-------------|
| Na | 0.89 | 0.89 | 0.92 | 0.87 |
| K  | 0.96 | 0.97 | 0.97 | 0.97 |
| P  | 0.93 | 0.93 | 0.91 | 0.94 |
| S  | 0.94 | 0.97 | 0.96 | 0.97 |
| F  | 0.93 | 0.93 | 0.96 | 0.90 |
| Cl | 0.98 | 0.98 | 0.97 | 0.99 |
| Br | 0.98 | 0.98 | 0.96 | 1.00 |
| I  | 0.97 | 1.00 | 1.00 | 1.00 |

MASS SPECTROMETRIC METHOD FOR DETERMINING THE PRESENCE OR ABSENCE OF A CHEMICAL ELEMENT IN AN ANALYTE

FIELD OF THE INVENTION

The present invention relates to mass spectrometric methods for determining the presence or absence of chemical elements in compounds.

BACKGROUND OF THE INVENTION

Mass spectrometry (MS) is a widely used analytical method for qualitative and quantitative identification of compounds in a wide variety of samples, including metabolomics, proteomics, pesticide analysis, natural compound identification, and pharmaceuticals. MS can be coupled to liquid/gas phase separation techniques, like liquid chromatography (LC) or gas-chromatography (GC). These hyphenated techniques LC/MS and GC/MS are extremely useful for detecting, identifying and quantifying of compounds within complex mixtures. In another hyphenated technique, MS or LC/MS is coupled with ion mobility spectrometry (IMS).

Mass spectrometry techniques comprise converting compounds of a sample into the gas phase, ionizing the compounds in an ion source, separating the molecular ions of the compounds according to mass-to-charge ratio in a mass analyzer and detecting the separated molecular ions. The mass-to-charge ratio is commonly denoted by the symbol "m/z" in which "m" is ion mass and "z" is the number of elementary charges of the molecular ion. Optionally, the molecular ions can be fragmented to form fragment ions which are then separated according to mass-to-charge ratio and detected.

There are many different types of ion sources, like chemical ionization, fast atom bombardment, matrix-assisted laser desorption/ionization (MALDI) and electrospray ionization (ESI), and of mass analyzers, like quadrupole mass filters, time-of-flight mass analyzers, time-of-flight mass analyzers with orthogonal ion injection, RF ion traps, DC ion traps (like an Orbitrap or Cassini-trap) and ion-cyclotron-resonance traps.

A measured mass spectrum comprises peaks (signals) of molecular ions and displays the mass-to-charge ratio of each peak on the abscissa with the corresponding relative intensity for the peak on the ordinate. Each peak is characterized by an m/z value and an intensity value (signal height).

The mass spectrum of molecular ions of a single compound exhibits a set of peaks with different m/z values due to the isotopes of the chemical elements. This set of (isotopic) peaks is termed the "isotopic pattern". Compounds with the same chemical formula exhibit the same isotopic pattern. The measured intensity of an isotopic peak correlates to the abundance of a specific molecular ion within the isotopic pattern of the compound. The relative intensities of the isotopic peaks are associated with the relative abundance of the isotopes.

The measured isotopic pattern of a compound can be used to annotate a chemical formula to the compound and often to identify the compound. While this is easily done for very small molecules, it quickly becomes a huge task for larger molecules.

A mass spectrum acquired for a complex mixture of compounds contains multiple isotopic patterns. Matching a measured isotopic pattern with respect to m/z and intensity values against a theoretically derived isotopic pattern for annotating a chemical formula to the corresponding compound is no trivial task. Initially, a set of isotopic patterns are calculated for a subsequent comparison with the measured isotopic pattern. Conceptually, this is done by convoluting the isotopic patterns of preselected chemical elements for all possible elemental combinations (chemical formulas) of these chemical elements which match the m/z value of the monoisotopic peak within a predetermined mass tolerance. For each one of the possible chemical formulas an isotopic pattern is calculated and compared with the measured isotopic pattern. This calculation can be done with different methods, such as Pearsons $\chi^2$ statistic.

However, the amount of possible chemical formulas becomes very large due to the combinatorics of the contained chemical elements. The number of possible chemical formulas around a specific m/z value and within a predetermined mass tolerance can be calculated for different sets of chemical elements. FIG. 1 shows the number of chemical formulas which are possible within a mass tolerance of 5 mDa in the m/z-range between 100 and 600 Da for three sets of chemical elements of interest ({C, H, N, O}, {C, H, N, O, P, S, NA, K, Cl}, {C, H, N, O, P, S, NA, K, Cl, BR, F, I}. The amount of possible chemical formulas grows exponentially. The more chemical elements are considered for generating the chemical formulas, the more chemical formulas are possible within the mass tolerance.

Since not all of the theoretically derived chemical formulas are chemically valid, a reduction of possible chemical formulas can be done by applying heuristic rules. However due to the exponential growths of possible chemical formulas with m/z, the number of remaining candidates can still be very large.

Current software tools usually rely on pattern comparison as described above. Adaptations to this approach have been made and new approaches are proposed to calculate isotopic patterns, for example using Markov-Chains, which reduce the computational cost by making tradeoffs. However, they do not address the exponential problem of possible chemical formulas. The set of chemical elements used for calculating the possible chemical formulas is at the core of the combinatorial problem. Providing or excluding certain elements beforehand reduces the amount of possible chemical formulas to be calculated and matched. Therefore, there is a need to determine (predict) chemical elements which are present in a compound to reduce the complexity during the annotation of a chemical formula to the compound.

SUMMARY OF THE INVENTION

The present invention provides a mass spectrometric method for determining the presence or absence of a chemical element in an analyte, comprising the steps:

(a) generating molecular ions of the analyte;
(b) measuring an isotopic pattern of the molecular ions by mass spectrometry, wherein the isotopic pattern comprises multiple isotopic peaks and each isotopic peak is characterized by a mass value and an intensity value;
(c) representing the isotopic pattern as a feature vector $\vec{v}$; and
(d) applying the feature vector $\vec{v}$ to a supervised element classifier that assigns the feature vector $\vec{v}$ to a first class (chemical element present) or to a second class (chemical element absent), wherein the supervised element classifier is trained on a set of feature vectors $\vec{v}_t$ which represent isotopic patterns of compounds with known elemental composition and wherein the chemical element is present in a proper subset of the compounds.

The set of compounds with known elemental composition comprises a proper subset of compounds in which the chemical element is present and a proper subset of known compounds in which the chemical element is absent, i.e. both subsets are not empty. Preferably, the compounds are distributed to both subsets by a ratio of at least 20/80. More preferably, the ratio is substantially 50/50. The molecular mass of these compounds is preferably smaller than 1000 Da, more preferably smaller than 600 Da, in particular between 100 and 600 Da. The mass spectrometric measurements of the analyte can for example be performed with a mass resolution $R \leq 100{,}000$, in particular with $R \leq 50{,}000$, more particular with $R \leq 25{,}000$.

The isotopic patterns used for training the supervised element classifier can be theoretically derived and/or experimentally measured. If the isotopic patterns of the compounds used for training the supervised element classifier are measured experimentally, the isotopic pattern of these compounds and the analyte are preferably measured on the same mass spectrometric system. However, isotopic patterns of known compounds which are collected in databases, e.g. in the KEGG database (Kyoto Encyclopedia of Genes and Genomes), can be used for selecting compounds containing the chemical element to be determined. The theoretically derived isotopic patterns can be selected by applying known chemical building rules to the corresponding chemical formulas, like the "Lewis-rule" and the "nitrogen-rule".

The chemical element to be determined is preferably one of Br, Cl, S, I, F, P, K, Na and Pt. The assignment in step (d) can be performed for multiple chemical elements by using different supervised element classifiers to achieve a multi-element determination. Preferably, the supervised element classifier inherently performs a multi-label classification for a set of two or more chemical elements. The assigned classes can also correspond to the presence or absence of a set of two or more chemical elements, wherein the supervised element classifier is trained on a set of feature vectors $\vec{v}_t$ which represent isotopic patterns of compounds with known elemental composition and wherein the two or more chemical elements are present in a proper subset of the compounds.

In a first embodiment, each one of the feature vectors $\vec{v}$ and $\vec{v}_t$ representing a corresponding isotopic pattern comprises mass values and normalized intensity values of the isotopic peaks. The feature vectors $\vec{v}$ and $\vec{v}_t$ preferably comprises a mass value of the monoisotopic peak, mass differences between the monoisotopic peak and other isotopic peaks and normalized intensity values of the isotopic peaks. More preferably, each one of the feature vectors $\vec{v}$ and $\vec{v}_t$ further comprises the mass difference between the monoisotopic peak and the nominal mass.

Each one of the feature vectors $\vec{v}$ and $\vec{v}_t$ can for example be arranged as follows: $[m_0, \bar{s}_0, d(m_0, m_1), \bar{s}_i, d(m_0, M_0)]$ with wherein $m_0$ is the mass value of the monoisotopic peak, $\bar{s}_0$ is the normalized intensity value of the monoisotopic peak, $d(m_0, m_1)$ is the mass difference between the monoisotopic peak and the ith isotopic peak, $\bar{s}_i$ is the normalized intensity value of the ith isotopic peak, and $d(m_0, M_0)$ is the difference between the mass value of the monoisotopic peak and the nominal mass $M_0$. The difference is preferably the result of a numerical subtraction, but can be a more general distance measure. N is preferably greater than 1, more preferably greater than 4, in particular equal to 9. For N=2 the feature vector looks like $[m_0, \bar{s}_0, d(m_0, m_1), \bar{s}_1, d(m_0, m_2), \bar{s}_2, d(m_0, M_0)]$.

The normalized intensity values $\bar{s}_i$ of a feature vector are calculated from the measured intensity values $s_i$ of corresponding isotopic peaks by using the p-norm:

$$\bar{s}_i = s_i / \|s\| \text{ with } \|s\| = (\Sigma |s_i|^p)^{1/p} \text{ with } 1 \leq p, \text{ in particular } p=1.$$

In a second embodiment, each one of the feature vectors $\vec{v}$ and $\vec{v}_t$ representing a corresponding isotopic pattern comprises mass values and transformed intensity values of the isotopic peaks. The intensity values of the isotopic peaks of the corresponding isotopic pattern are preferably transformed by a centered-log ratio transformation (clr-transformation) or by an isometric log-ratio transformation (ilr-transformation).

For the clr-transformation, each one of the feature vectors $\vec{v}$ and $\vec{v}_t$ can for example be arranged as follows:

$$[m_0, clr_0, d(m_0, m_i), clr_i, d(m_0, M_0)] \text{ with } i=1 \ldots N,$$

wherein $m_0$ is the mass value of the monoisotopic peak, $clr_0$ is the clr-transformed intensity value of the monoisotopic peak, $d(m_0, m_1)$ is the mass difference between the monoisotopic peak and the ith isotopic peak, $clr_i$ is the clr-transformed intensity value of the ith isotopic peak, and $d(m_0, M_0)$ is the difference between the mass value of the monoisotopic peak and the nominal mass and wherein the clr-transformation is defined by:

$$clr_i = \log(s_i / (s_0 \cdot s_1 \cdots s_N)^{1/(N+1)}) \text{ with } s_{i=0 \ldots N} \text{ being the intensity values of the isotopic peaks.}$$

N is preferably greater than 1, more preferably greater than 4, in particular equal to 9. For N=2 the feature vector looks like $[m_0, clr_0, d(m_0, m_1), clr_1, d(m_0, m_2), clr_2, d(m_0, M_0)]$.

For the ilr-transformation, each one of the feature vectors $\vec{v}$ and $\vec{v}_t$ can for example be arranged as follows:

$$[m_0, ilr_0, d(m_0, m_i), ilr_i, d(m_0, m_N), d(m_0, M_0)] \text{ with } i=1 \ldots N-1,$$

wherein $m_0$ is the mass value of the monoisotopic peak, $ilr_i$ are the ilr-transformed intensity values of the isotopic peaks, $d(m_0, m_i)$ is the mass difference between the monoisotopic peak and the ith isotopic peak, and $d(m_0, M_0)$ is the difference between the mass value of the monoisotopic peak and the nominal mass and wherein the ilr-transformation is defined by:

$$\vec{ilr} = \vec{clr} \cdot \underline{B} \text{ with } \vec{ilr} = (ilr_{i=0 \ldots N-1}), \vec{clr} = (clr_{i=0 \ldots N}),$$
balance matrix $\underline{B}$ of reduced dimension
$dim(\underline{B}) = (N+1) \times N$ and $\underline{B} \cdot \underline{B}^T = \underline{I}_N$ N is preferably greater than 1, more preferably greater than 4, in particular equal to 9. For N=2 the feature vector looks like $[m_0, ilr_0, d(m_0, m_1), ilr_1, d(m_0, m_2), d(m_0, M_0)]$.

The supervised element classifier can for example be one of a support vector machine (SVM), an artificial neural network (NN), e.g. convolutional neural network (CNN) or a Long-Short-Term-Memory Networks (LSTMN), or a random forest classifier (RF, random decision forest). The inherent parameters of the supervised element classifier (hyperparameters) are preferably optimized during the training of the supervised element classifier, e.g. by using one of swarm optimization, evolutionary algorithm, genetic algorithm, multi-start optimization, simulated annealing and pattern search. The hyperparameters generally depend on how the isotopic pattern is represented as feature vector, i.e.

for example on the selected features, the length of the feature vector, the normalization/transformation of the intensity values, the representation of the m/z values and arrangement of features inside the feature vector.

The presentation of the isotopic pattern as a feature vector is preferably optimized during the training of the supervised element classifier. The representation can for example be optimized with regard to the dimension of the feature vector, the normalization or transformation of the measured intensity values, the arrangement of the components of the feature vector. A feature selection or estimation of feature importance can also be part of the optimization and performed during the training of the supervised element classifier, e.g. by the LASSO algorithm (Least Absolute Shrinkage and Selection Operator) or RF algorithm (Random Forest).

The isotopic pattern of the analyte is preferably measured by a mass analyzer which is coupled to an upstream ion mobility analyzer and/or to a gas or liquid chromatograph. Preferably, the mass analyzer is a time-of-flight mass analyzer with orthogonal ion injection (OTOF). More preferably, the OTOF is coupled to an ion mobility mass analyzer, in particular to a TIMS analyzer (Trapped Ion Mobility Spectrometry).

In a further aspect, the result of determining the presence or absence of a chemical element according to the present invention is used for reducing or enhancing the number of chemical elements considered during annotating a chemical formula to the analyte, in particular during calculating the set of isotopic patterns for the subsequent comparison with the measured isotopic pattern. The isotopic pattern of the analyte ions is preferably measured during an LC- or GC-separation, more preferably during a coupled LC-IMS or GC-IMS-separation.

DETAILED DESCRIPTION OF THE INVENTION

Figure 1:
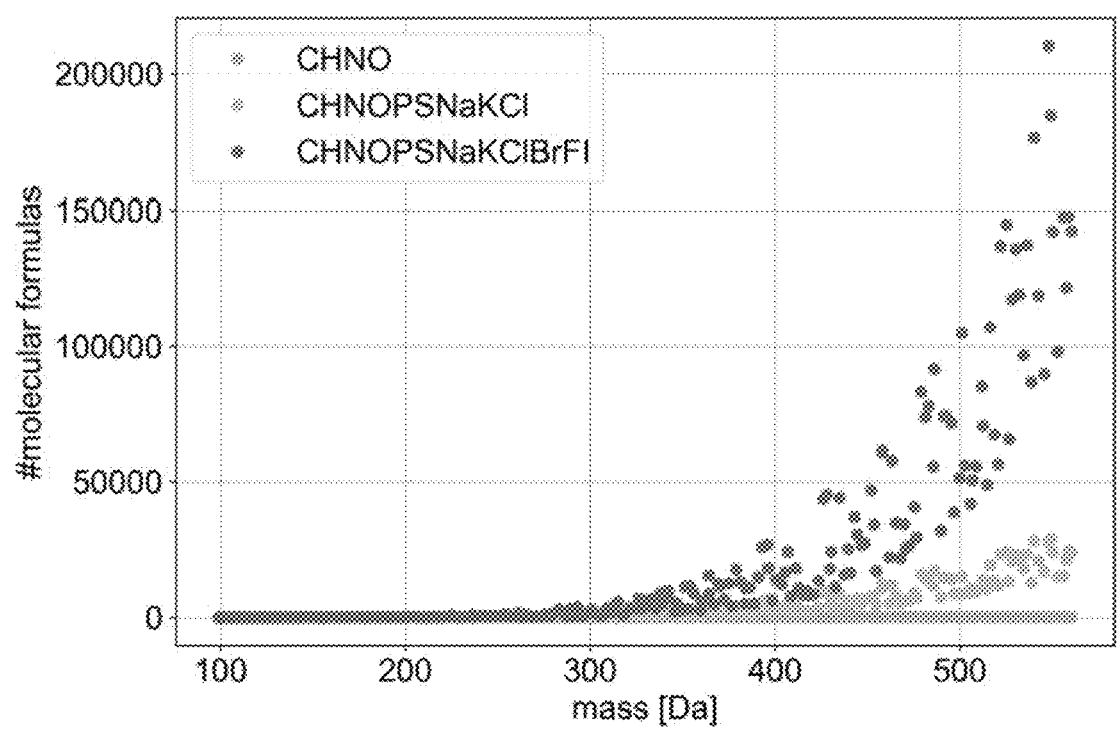
FIG. 1 shows the number of chemical formulas within a mass tolerance of 5 mDa in the m/z-range between 100 and 600 Da for three sets of chemical elements ({C, H, N, O}, {C, H, N, O, P, S, NA, K, Cl}, {C, H, N, O, P, S, Na, K, Cl, Br, F, I}.
Figure 2:
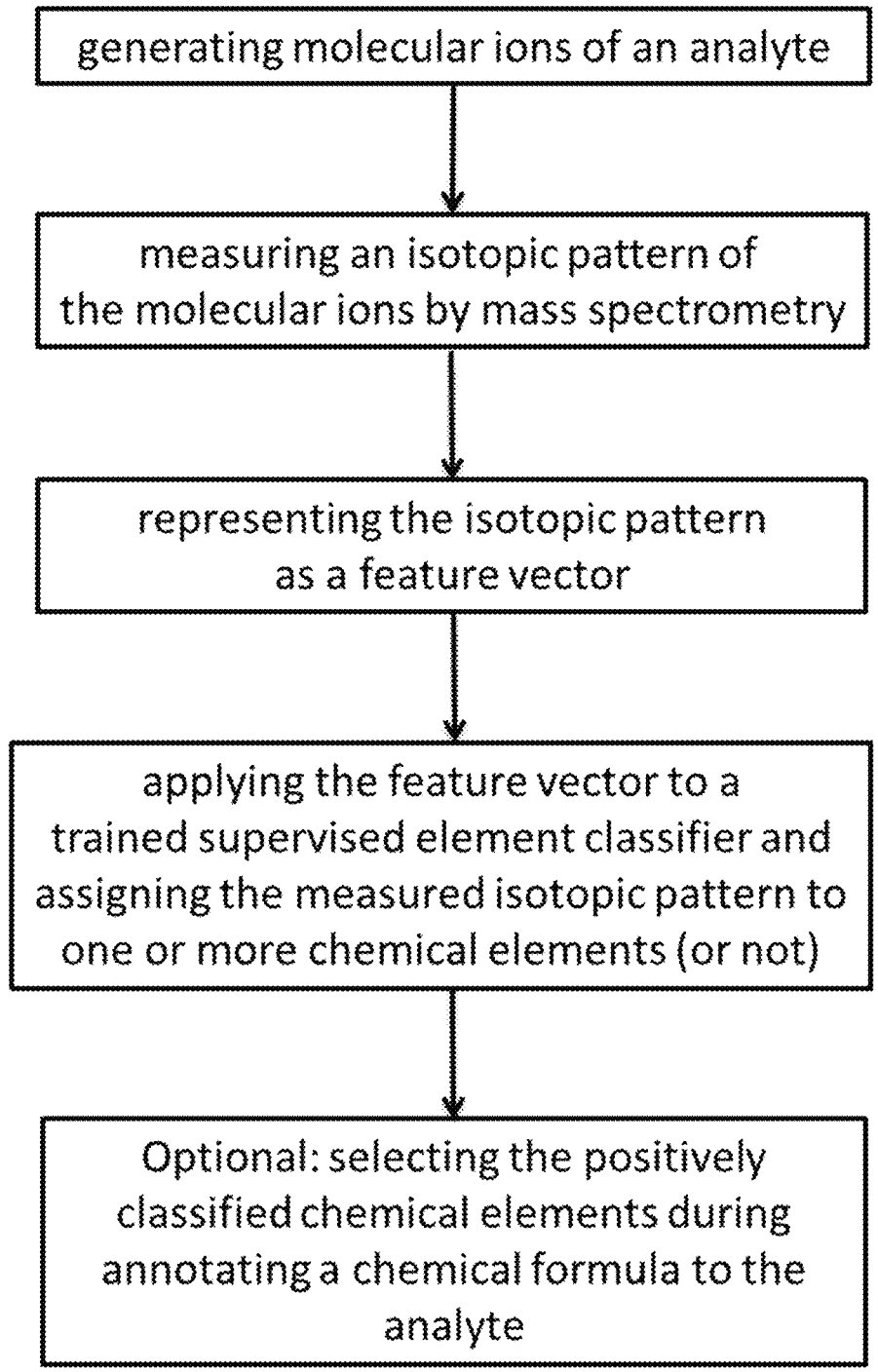
FIG. 2 shows a flow chart of a method according to the present invention.

While the invention has been shown and described with reference to a number of different embodiments thereof, it will be recognized by those skilled in the art that various changes in form and detail may be made herein without departing from the scope of the invention as defined by the appended claims.

Elemental composition is at the core of the combinatorial problem for generating possible chemical formulas for a given m/z-value. It is a goal of the present invention to predict chemical elements that are contained in an analyte from the measured isotopic pattern of the analyte and thus to determine the elemental composition of the analyte used for a subsequent generation of possible chemical formulas. Providing or excluding certain chemical elements reduces the amount of possible chemical formulas to be calculated and compared. According to the present invention, machine learning by using supervised classifier provides a way to solve this problem.

In addition to reducing complexity of the annotating procedure, the method according to the present invention allows to specifically select and examine only certain isotopic pattern and thus compounds of interest, based on the presence of specific chemical elements.

Definitions

The term "mass value" is used here interchangeably for the mass-to-charge ratio (m/z value) of a molecular ion as well as for the molecular mass of the corresponding compound. The mass-to-charge ratio of a molecular ion can be converted to the molecular mass of the corresponding compound, e.g. by charge deconvolution.

The "nominal mass" for a chemical element is the mass number of its most abundant naturally occurring stable isotope. For a molecular ion or molecule, the nominal mass is the sum of the nominal masses of the constituent atoms. For example, carbon has two stable isotopes $12C$ at 98.9% natural abundance and 13C at 1.1% natural abundance, thus the nominal mass of carbon is 12.

The mass of the "monoisotopic peak" is the sum of the masses of the atoms in a molecule using the mass of the principal (most abundant) isotope for each chemical element. The difference between the nominal mass and the monoisotopic mass is termed mass defect.

A "confusion matrix" is a table that allows visualization of the performance of a classifier, typically a supervised classifier. Each row of the confusion matrix represents the instances in a predicted class while each column represents the instances in an actual class:

|  | Positive Condition | Negative Condition |  |
| --- | --- | --- | --- |
| Positive Prediction | TP (True Positive) | FP (False Positive) | Positive predictive value $$PPV = \frac{\sum TP}{\sum TP + FP}$$ |
| Negative Prediction | FN (False Negative) | TN (True Negative) | Negative predictive value $$NPV = \frac{\sum TN}{\sum TN + FN}$$ |
|  | $Sensitivity = \frac{\sum TP}{\sum TP + FN}$ | $Specificity = \frac{\sum TN}{\sum TN + FP}$ |  |

Support-Vector Machine (SVM):

A support-vector machine (SVM) is a supervised machine learning method which can be used for classification. During training, a SVM constructs a hyperplane in the highly dimensional data space which separates labeled training data points with respect to their class labels. The parameters of the hyperplane are optimized such that the distance to the nearest training-data points of any class (so-called margin) is maximized. An important consequence of this geometric description is that the max-margin hyperplane is completely determined by those data points that lie nearest to it. These data points are called support vectors. An assignment of unlabeled data points to be classified after training is made by determining on which side the unlabeled data points are located. Once trained properly, unlabeled data points can be assigned to a class at fast speed and low computational effort.

The SVM can be extended to cases in which the data are not linearly separable, for example by introducing a so called "soft-margin". The "soft-margin" allows that training data points are not accurately separated by the margin. An internal untrained parameter (hyperparameter) of the SVM determines a trade-off between increasing the margin and ensuring that all training data points lie on the correct side of the margin.

The SVM can further be generalized by applying a so-called kernel trick by which the data points of the input space are transformed into a transformed feature space. The transformation allows fitting a maximum-margin hyperplane in the transformed feature space. The transformation can be nonlinear and the transformed feature space higher-dimensional than the input space. Although the classifier is based on a separating hyperplane in the transformed feature space, it may be nonlinear in the original input space. The nonlinear kernel function can further comprise additional hyperparameters (untrained, predetermined parameters). Functions of common kernels include for example polynomials (homogeneous or inhomogeneous), radial-basis functions (RBF) and hyperbolic tangent functions.

Artificial Neural Network (ANN)

An artificial neural network (ANN) is a system inspired by biological neural networks. An ANN is generally based on a collection of connected nodes (artificial neurons). Each connection (edge) between artificial neurons, like the synapses in a biological neural network, can transmit a signal from one artificial neuron to another. An artificial neuron that receives a signal can process it and then signal additional artificial neurons connected to it. The output of each artificial neuron is computed by some non-linear function (activation function) of the sum of its inputs. Artificial neurons may have a threshold such that the signal is sent only if the sum of the inputs is above that threshold.

Typically, artificial neurons are aggregated into layers. Different layers may perform different kinds of transformations on their inputs. Signals travel from the first layer (the input layer), to the last layer (the output layer), possibly after traversing multiple hidden layers.

The connections between artificial neurons typically have weights that are adjusted during training. The weight increases or decreases the strength of the signal at a connection. Numerous algorithms are available for training neural network models. Most of them can be viewed as an optimization employing some form of gradient descent and using backpropagation to compute the actual gradients.

An artificial neural network generally comprises multiple hyperparameters, in particular more hyperparameters than a SVM. Hyperparameters of an artificial neural network can be related to the structure of the network itself, e.g. the number of the hidden layers, the number of the nodes, biases of nodes or layers, as well as to parameters of the activation function of the nodes and a regularizing parameter which penalizes the decision boundary in case of overfitting.

Example 1

Here, the supervised element classifier is a support vector machine (SVM) using a "soft margin" and an RBF kernel. The hyperparameters are related to the "soft margin" and the RBF kernel, and are optimized during the training by particle swarm optimization. The isotopic patterns used for training and validating the SVM are experimentally measured.

The experimental data are obtained from measurements on an OTOF mass spectrometer with an electrospray source which is coupled to a liquid chromatograph. The compounds with known elemental composition belong to different compound classes: coffee metabolomics, synthetic molecules, pesticides and toxic substances.

Figure 3:
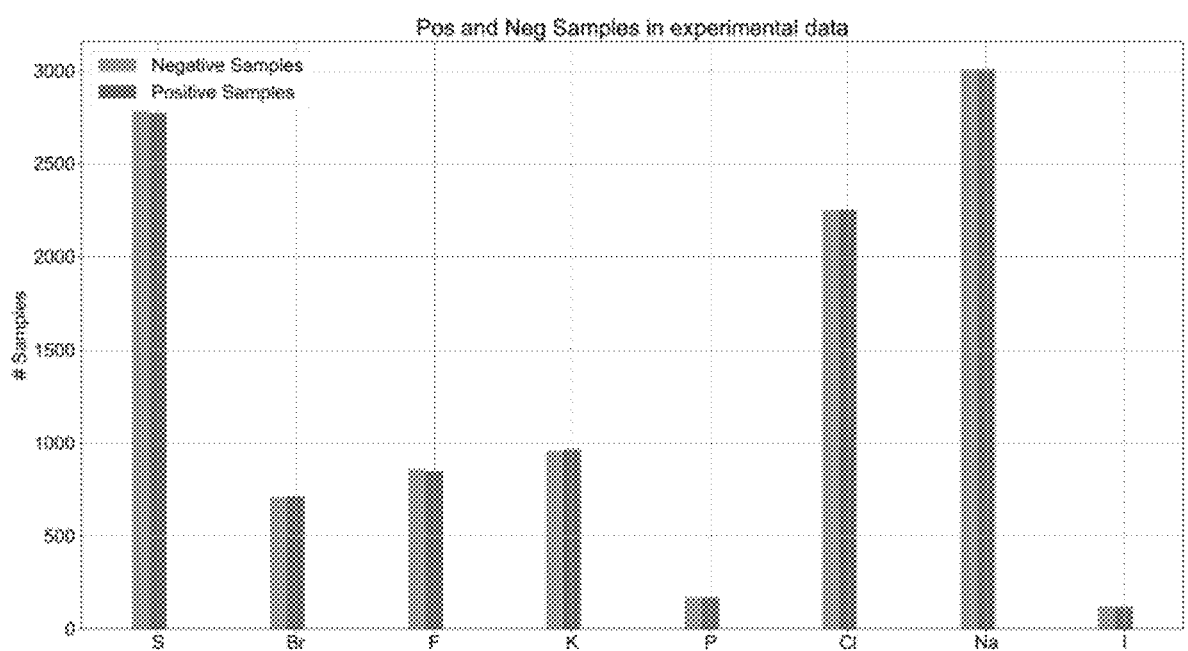
FIG. 3 shows the number of experimentally measured compounds (positive and negative) for the chemical elements of interest prepared in equal amounts to be used for training and validation. The data set is split 80%/20% for training and validation of the supervised element classifiers.

The element determination is applied only to compounds with a molecular mass below 600 Da. The training data set is balanced with equal amounts of compounds containing an element (positive) and not containing an element (negative). The chemical elements of interest are: Br, Cl, S, I, F, P, K and Na. The elements C, H, N and O are almost always present and therefore are not part of the classification. The choice for elements of interest is based on their occurrence in the experimental data and a vast majority of biomolecules. FIG. 3 shows the number of compounds (positive and negative) for the chemical elements of interest to be used for training and validation of the SVM. The data set is split for training (80%) and validation (20%). The number of compounds used for validation are:

| Na | K | P | S | F | Cl | Br | I |
|---|---|---|---|---|---|---|---|
| 1204 | 384 | 68 | 1110 | 338 | 900 | 284 | 48 |

The isotopic patterns are represented in three different ways by using a p-normalization with p=1 (closure), a centered-log ratio transformation (clr) and an isometric log-ratio transformation (ilr). For closure and clr-representation, the feature vectors are arranged as follows: $[m_0, \ln t_0, m_i-m_0, \ln t_i, mDef]$ with i=1 ... 9, wherein $m_0$ and $m_i$ are the mass values isotopic peaks, mDef is the mass defect and $\ln t_0$ and $\ln t_i$ are the normalized or transformed intensity values calculated from the measured intensity values $s_i$. For ilr-representation, the feature vector does not comprise a $\ln t_9$ component. The length of the feature vectors is 21 (closure and clr) and 20 (ilr). The hyperparameters of the SVM are separately optimized for each representation.

Figure 4:
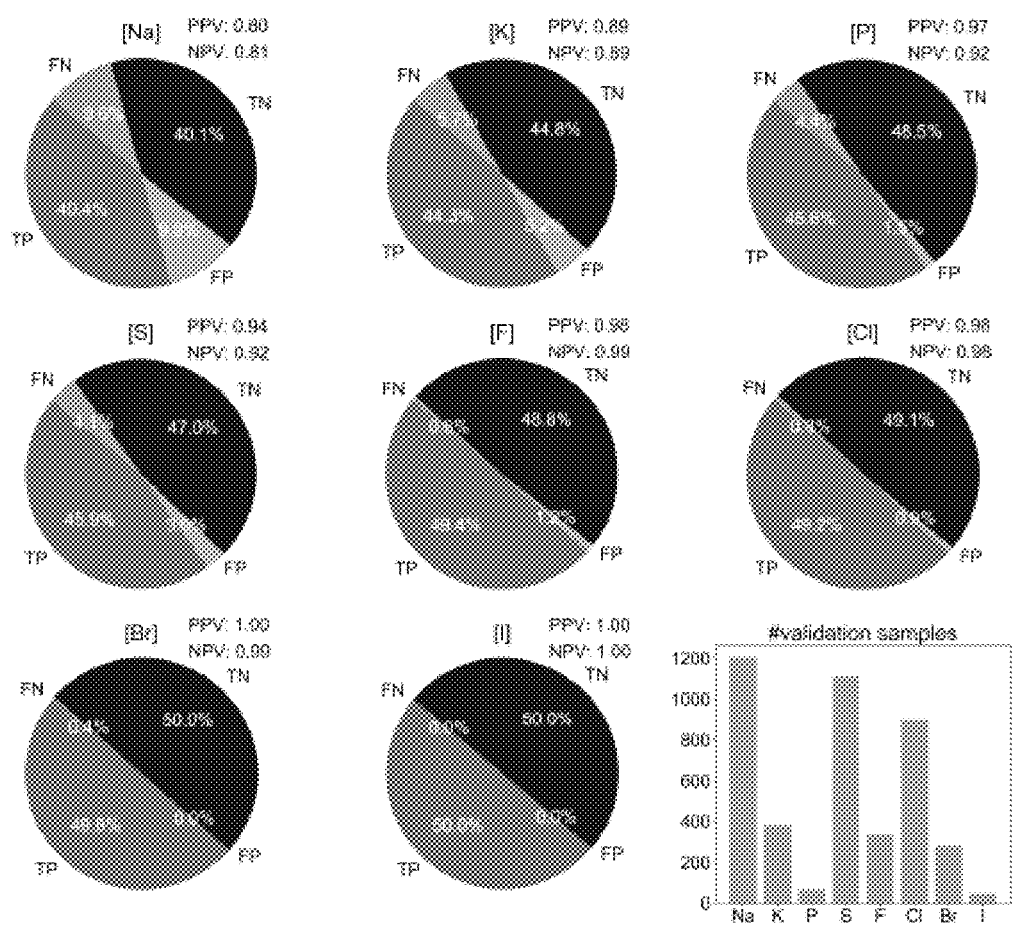
FIG. 4 shows results for a smart-margin RBF-Kernel SVM trained on the experimental data and optimized by particle swarm optimization. The measured intensity values of the isotopic patterns are normalized by p-norm with p=1 (closure). The results comprise accuracy of correct classification, sensitivity, specificity and the complete confusion matrix.
Figure 5:
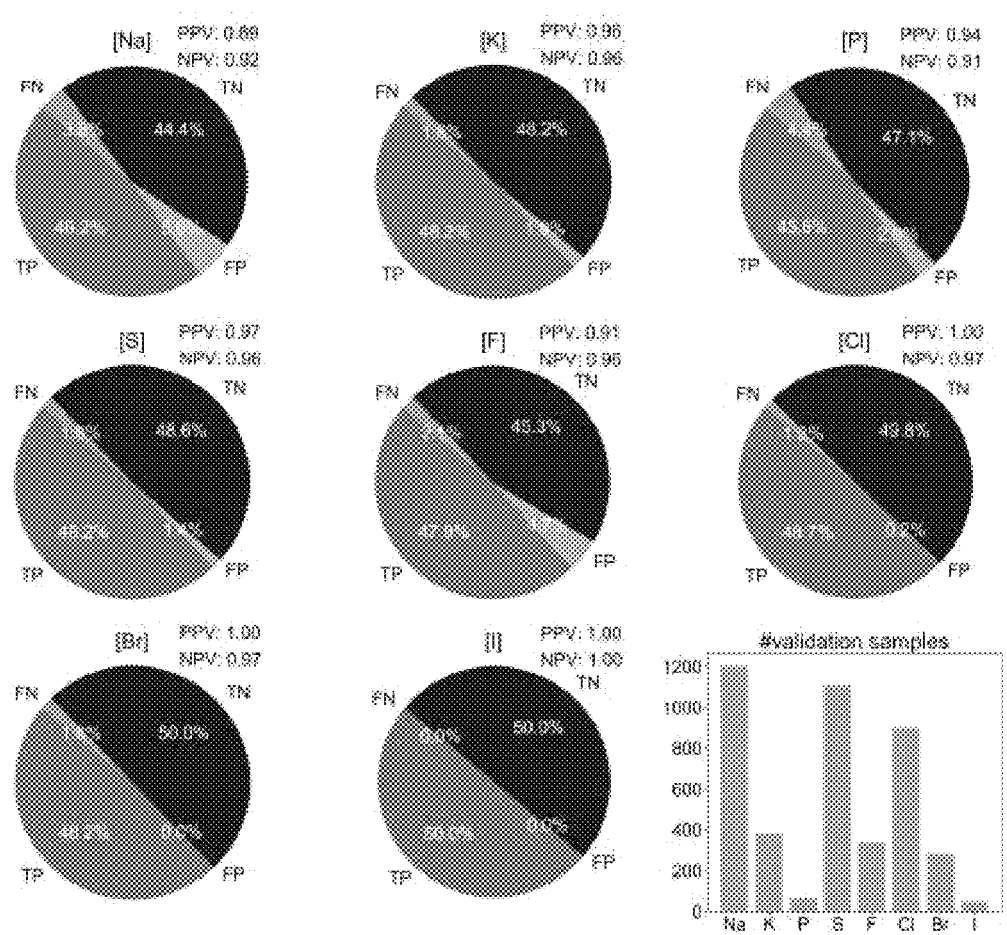
FIG. 5 shows results for a smart-margin RBF-Kernel SVM trained on the experimental data and optimized by particle swarm optimization. The measured intensity values of the isotopic patterns are transformed by a centered-log ratio (clr) transformation. The results comprise accuracy of correct classification, sensitivity, specificity and the complete confusion matrix.
Figure 6:
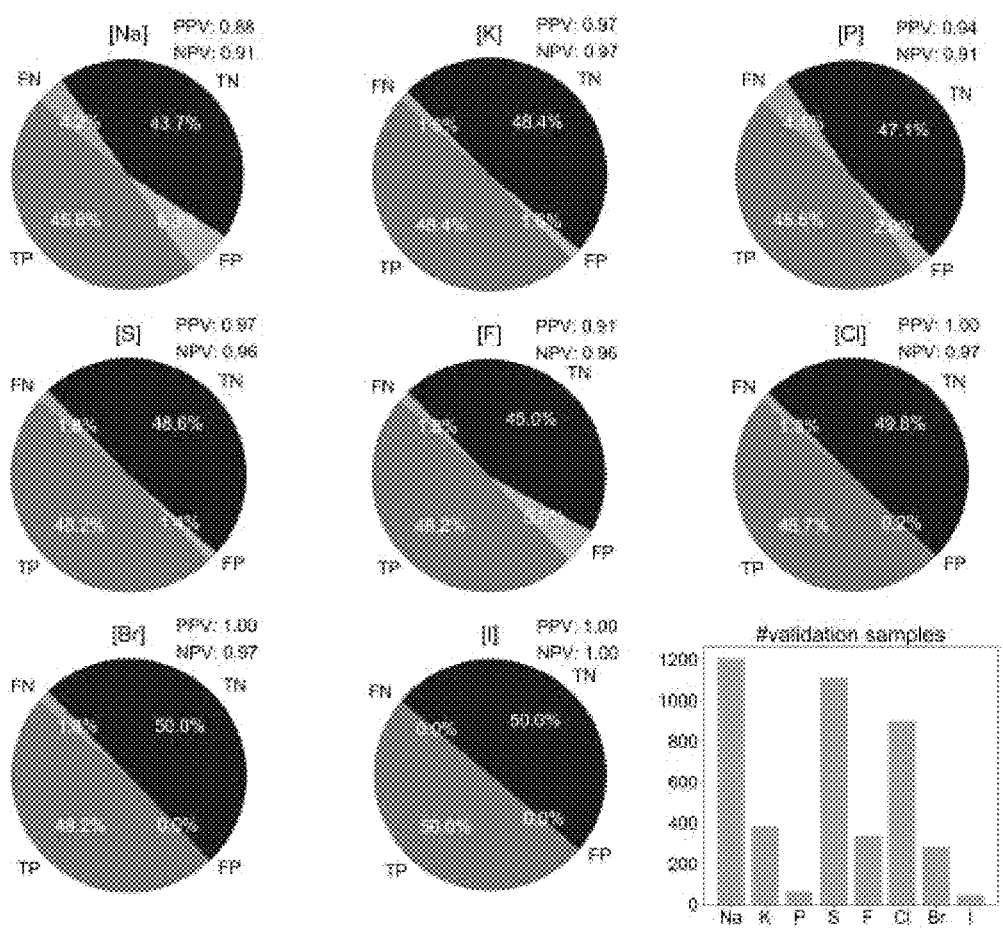
FIG. 6 shows results for a smart-margin RBF-Kernel SVM trained on the experimental data and optimized by particle swarm optimization. The measured intensity values of the isotopic patterns are transformed by an isometric log-ratio (ilr) transformation. The results comprise accuracy of correct classification, sensitivity, specificity and the complete confusion matrix.

FIGS. 4 to 6 show results for the smart-margin RBF-Kernel SVM trained on the experimental data and optimized by particle swarm optimization. The results comprise accuracy of correct classification, sensitivity, specificity and the complete confusion matrix. In FIG. 4, the measured intensity values of the isotopic patterns are normalized by p-norm with p=1 (closure). In FIG. 5, the measured intensity values of the isotopic patterns are transformed by a centered-log ratio transformation (clr). In FIG. 6, the measured intensity values of the isotopic patterns are transformed by an isometric log-ratio transformation (ilr).

Example 2

Figure 7:
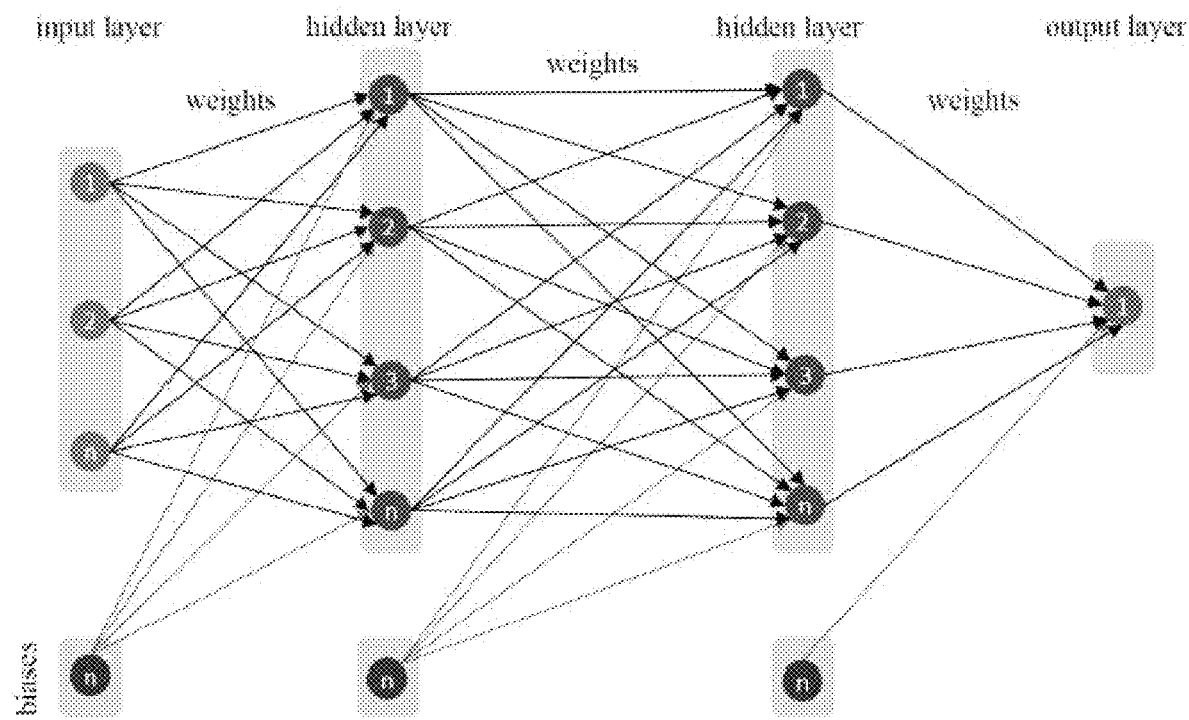
FIG. 7 shows a schematic of a dense, feed-forward neural network with biases. Numbers in the neurons depict the index of the neurons and do not represent their values.

Here, the supervised element classifier is a dense, feed-forward, artificial neural network ANN with biases, as shown in FIG. 7. In a dense network, each layer is fully connected to the following layer. The activation function of the ANN is a rectified linear unit:

$$ReLU(x) = \begin{cases} x & \text{if } x > 0 \\ 0 & \text{if } x \leq 0 \end{cases}.$$

The predictions for the validation data set are made by a feed-forward pass through the ANN.

The isotopic patterns used for training and validating the ANN are experimentally measured. The experimental data and the representation of the isotopic pattern are the same as in Example 1.

During training, the feature vectors are submitted to the ANN in batches. A batch is a subset of all feature vectors used for training the ANN. Once a batch has been passed through the ANN, a back-propagation takes place. It propagates the error of the current prediction back through the ANN in order to update the weights by adjusting their values in small steps towards the best gradient. The weights are adjusted for a given set of hyperparameters.

The hyperparameters of the ANN are a regularizing parameter, the number of hidden layers and the number of artificial neurons in the hidden layers. An evolutionary algorithm is used to optimize the hyperparameters of the ANN.

Figure 8:
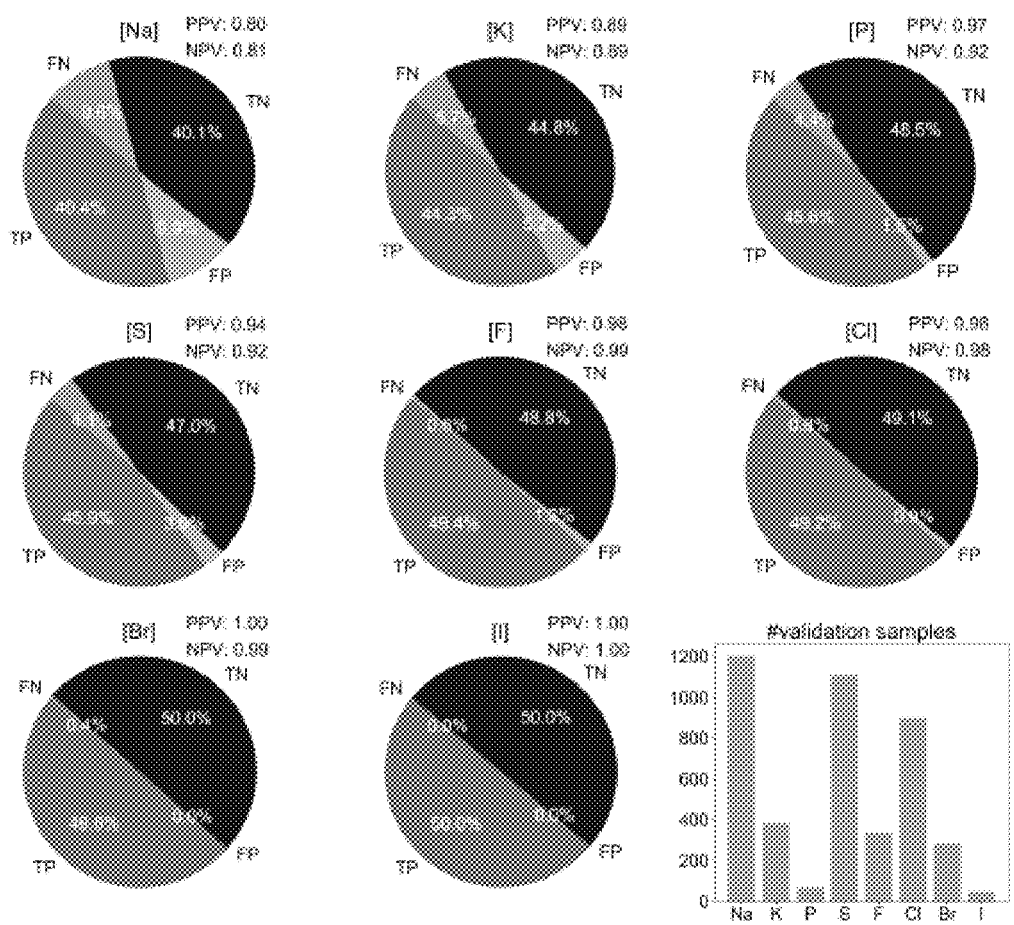
FIG. 8 shows results for a dense, feed-forward artificial neural network trained on the experimental data and optimized by an evolutionary algorithm. The measured intensity values of the isotopic patterns are normalized by p-norm with p=1 (closure). The results comprise accuracy of correct classification, sensitivity, specificity and the complete confusion matrix.
Figure 9:
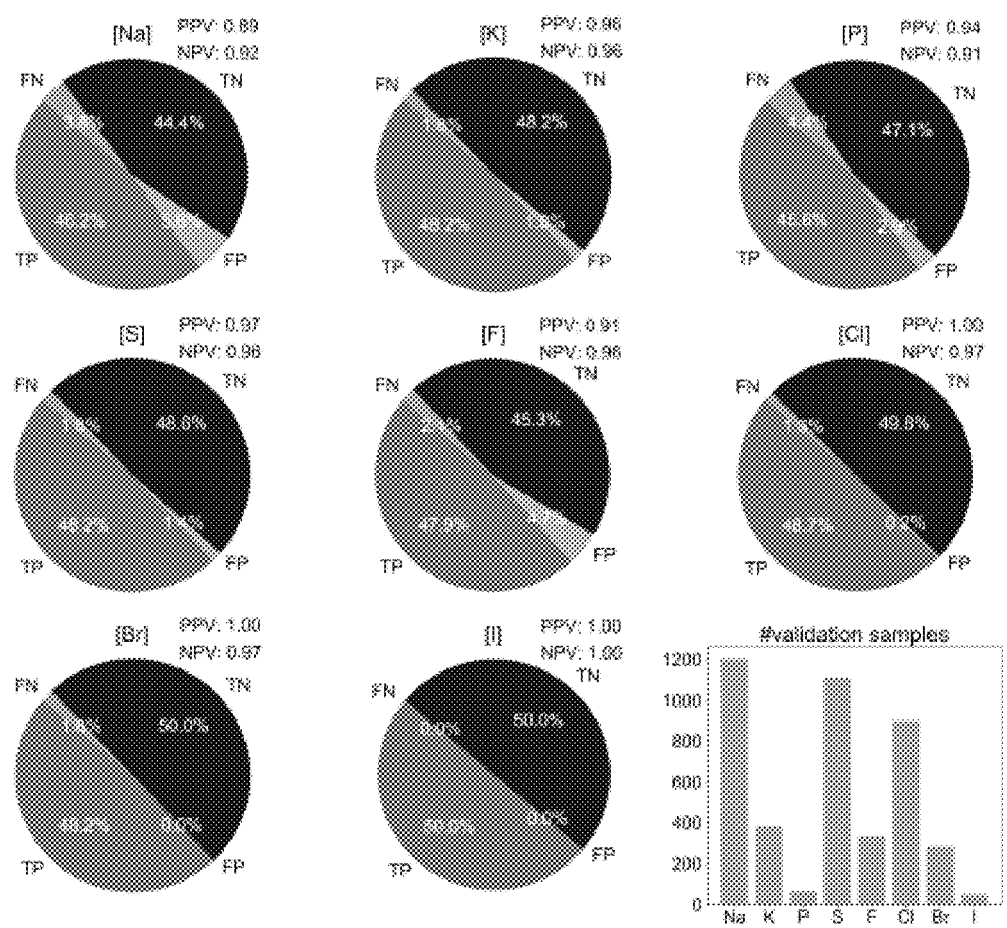
FIG. 9 shows results for a dense, feed-forward artificial neural network trained on the experimental data and optimized by an evolutionary algorithm. The measured intensity values of the isotopic patterns are transformed by a centered-log ratio (clr) transformation. The results comprise accuracy of correct classification, sensitivity, specificity and the complete confusion matrix.
Figure 10:
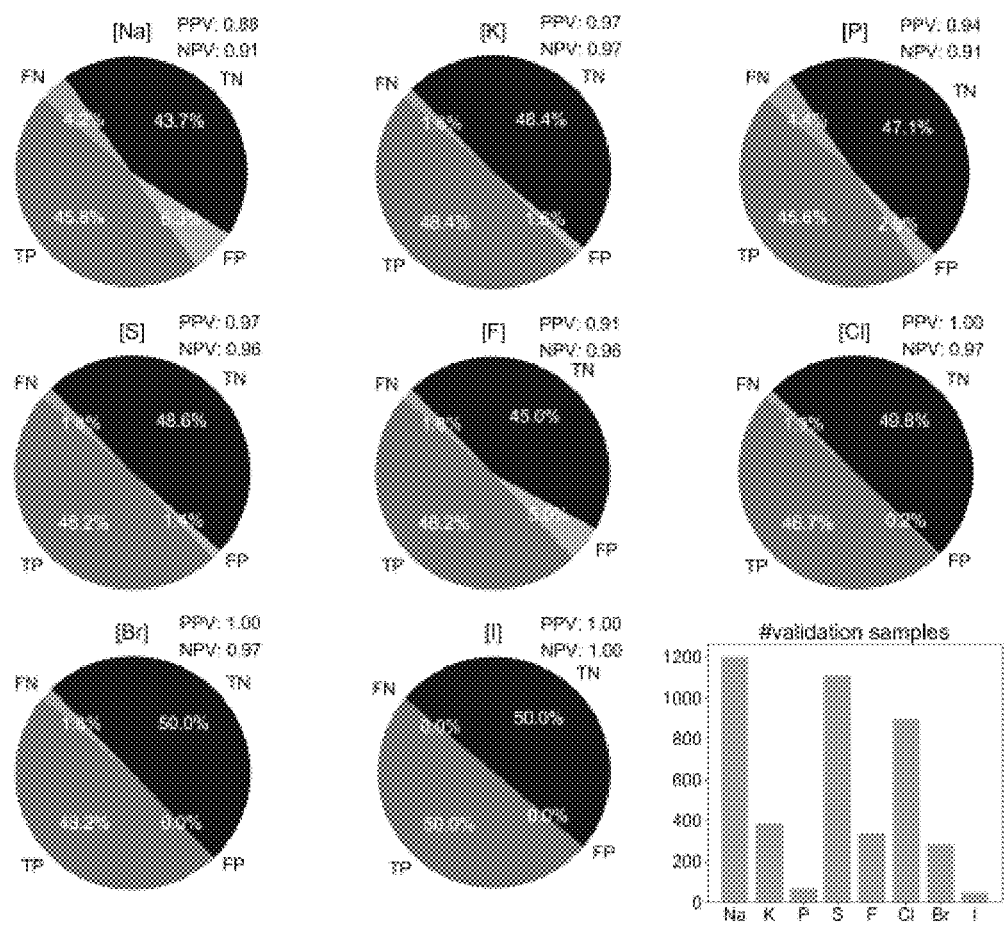
FIG. 10 shows results for a dense, feed-forward artificial neural network trained on the experimental data and optimized by an evolutionary algorithm. The measured intensity values of the isotopic patterns are transformed by an isometric log-ratio (ilr) transformation. The results comprise accuracy of correct classification, sensitivity, specificity and the complete confusion matrix.

FIGS. 8 to 10 show results for the ANN. The results comprise accuracy of correct classification, sensitivity, specificity and the complete confusion matrix. In FIG. 8, the measured intensity values of the isotopic patterns are normalized by p-norm with p=1 (closure). In FIG. 9, the measured intensity values of the isotopic patterns are transformed by a centered-log ratio transformation (clr). In FIG. 10, the measured intensity values of the isotopic patterns are transformed by an isometric log-ratio transformation (ilr).

The results of both examples show that the machine learning algorithms used achieve good prediction results for element prediction from mass spectrometric signals. The SVM works better than the ANN. The prediction for poly-isotopic chemical elements is generally more accurate than the prediction for single isotopic chemical elements.

Considering the use case of reducing chemical elements during the annotation of a chemical formula to a measured analyte, it is possible to remove elements from consideration if so predicted. However, removal of an element from consideration that is present in the underlying analyte during the annotation needs to be prevented. Otherwise a correct match cannot be found. For this use case the negative predictive value (NPV) of a classifier is important. It refers to the percentage of correct negative prediction under negative condition.

The SVM classifier shows a NPV of 89-100% for the polyisotopic chemical elements. The NPV for the ANNs is generally worse.

For the reversed use case of suggesting elements during the annotation of chemical formulas to a measured analyte, the positive predictive value (PPV) is of importance. PPV refers to percentage of correct positive prediction under positive condition. However, suggesting a chemical element that is not part of the underlying analyte results in addition of false positive chemical formulas and increases the overall complexity. Therefore a classifier for this use case needs to have a high PPV value.

The SVM classifier shows a PPV≥89% for the polyisotopic chemical elements. The PPV for the ANNs is generally worse.

The invention has been shown and described above with reference to a number of different embodiments thereof. It will be understood, however, by a person skilled in the art that various aspects or details of the invention may be changed, or various aspects or details of different embodiments may be arbitrarily combined, if practicable, without departing from the scope of the invention. Generally, the foregoing description is for the purpose of illustration only, and not for the purpose of limiting the invention which is defined solely by the appended claims, including any equivalent implementations, as the case may be.

The invention claimed is:

1. A mass spectrometric method for determining the presence or absence of a chemical element in an analyte, the method comprising:
   (a) generating analyte ions from the analyte;
   (b) measuring an isotopic pattern of the analyte ions by mass spectrometry, wherein the isotopic pattern comprises multiple isotopic peaks each characterized by a mass value and an intensity value;
   (c) representing the isotopic pattern as a feature vector $\vec{v}$; and
   (d) applying the feature vector $\vec{v}$ to a supervised element classifier that assigns the feature vector $\vec{v}$ to a first class indicative of the chemical element being present or to a second class indicative of the chemical element being absent, wherein the supervised element classifier is trained on a set of feature vectors $\vec{v}_t$ which represent isotopic patterns of compounds with known elemental composition and wherein the chemical element is present in a proper subset of the compounds.

2. The method according to claim 1, wherein each of the feature vector $\vec{v}$ and the feature vectors of the set $\vec{v}_t$ representing a corresponding isotopic pattern comprises mass values and normalized intensity values of the isotopic peaks of its respective isotopic pattern.

3. The method according to claim 1, wherein each of the feature vector $\vec{v}$ and the feature vectors of the set $\vec{v}_t$ representing a corresponding isotopic pattern comprises a mass value of a monoisotopic peak, mass differences between the monoisotopic peak and other isotopic peaks and normalized intensity values of the isotopic peaks of its respective isotopic pattern.

4. The method according to claim 3, wherein each of the feature vector $\vec{v}$ and the feature vectors of the set $\vec{v}_t$ further comprises a mass difference between the monoisotopic peak and a nominal mass.

5. The method according to claim 4, wherein each of the feature vector $\vec{v}$ and the feature vectors of the set $\vec{v}_t$ is arranged as follows: $[m_0, \bar{s}_0, d(m_0, m_i), \bar{s}_i, d(m_0, M_0)]$ with $i=1 \ldots N$, wherein $m_0$ is the mass value of the monoisotopic peak, $\bar{s}_0$ is a normalized intensity value of the monoisotopic peak, $d(m_0, m_i)$ is a mass difference between the monoisotopic peak and the ith isotopic peak, $\bar{s}_i$ is a normalized intensity value of an ith isotopic peak, and $d(m_0, M_0)$ is a difference between the mass value of the monoisotopic peak and nominal mass $M_0$.

6. The method according to claim 2, wherein normalized intensity values $\bar{s}_i$ of a feature vector are calculated from intensity values $s_i$ of corresponding isotopic peaks by using a p-norm:

$$\bar{s}_i = s_i / \|s\| \text{ with } \|s\| = (\Sigma |s_i|^p)^{1/p} \text{ with } 1 \leq p.$$

7. The method according to claim 1, wherein each of the feature vector $\vec{v}$ and the feature vectors of the set $\vec{v}_t$ representing a corresponding isotopic pattern comprises mass values and transformed intensity values of the isotopic peaks of its respective isotopic pattern.

8. The method according to claim 7, wherein the intensity values of the isotopic peaks of said corresponding isotopic pattern are transformed by a centered-log ratio (clr) transformation or by an isometric log-ratio (ilr) transformation.

9. The method according to claim 8, wherein each of the feature vector $\vec{v}$ and the feature vectors of the set $\vec{v}_t$ is arranged as follows: $[m_0, clr_0, d(m_0, m_i), clr_i, d(m_0, M_0)]$ with $i=1 \ldots N$,
wherein $m_0$ is the mass value of a monoisotopic peak, $clr_0$ is a clr-transformed intensity value of the monoisotopic peak, $d(m_0, m_i)$ is a mass difference between the monoisotopic peak and an ith isotopic peak, $clr_i$ is a clr-transformed intensity value of the ith isotopic peak, and $d(m_0, M_0)$ is a difference between the mass value of the monoisotopic peak and a nominal mass and wherein the clr-transformation is defined by:

$$clr_i = \log(s_i / \sqrt[N+1]{s_0 \cdot s_1 \cdots s_N}) \text{ with } s_{i=0 \ldots N} \text{ being the intensity values of the isotopic peaks.}$$

10. The method according to claim 8, wherein each of the feature vector $\vec{v}$ and the feature vectors of the set $\vec{v}_t$ is arranged as follows: $[m_0, ilr_0, d(m_0, m_i), ilr_i, d(m_0, m_N), d(m_0, M_0)]$ with $i=1 \ldots N-1$,
wherein $m_0$ is the mass value of a monoisotopic peak, $ilr_i$ are the ilr-transformed intensity values of the isotopic peaks, $d(m_0, m_i)$ is a mass difference between the monoisotopic peak and a ith isotopic peak, and $d(m_0, M_0)$ is a difference between the mass value of the monoisotopic peak and a nominal mass and wherein the ilr-transformation is defined by:

$$\vec{ilr} = \vec{clr} \cdot \underline{B} \text{ with } \vec{ilr} = (ilr_{i=0 \ldots N-1}), \vec{clr} = (clr_{i=0 \ldots N}),$$
and balance matrix $\underline{B}$ of reduced dimension
$dim(\underline{B}) = (N+1) \times N$ and $\underline{B} \cdot \underline{B}^T = \underline{I}_N$.

11. The method according to claim 1, wherein the supervised element classifier is one of a support vector machine (SVM), an artificial neural network (NN) and a random forest (RF, random decision forest) classifier.

12. The method according to claim 11, wherein the inherent parameters of the supervised element classifier (hyperparameter) are optimized during the training of the supervised element classifier.

13. The method according to claim 1, wherein the presentation of the isotopic pattern as a feature vector is optimized during the training of the supervised element classifier.

14. The method according to claim 13, wherein a selection of features or estimation of feature importance is performed during the training of the supervised element classifier.

15. The method according to claim 1, wherein the chemical element is one of Br, Cl, S, I, F, P, K, Na and Pt.

16. The method according to claim 15, wherein, in step (d), the first class corresponds to the presence of two or more of the chemical elements and the second class corresponds to the absence of said two or more of the chemical elements and wherein the supervised element classifier is trained on a set of feature vectors $\vec{v}_t$ which represent isotopic patterns of compounds with known elemental composition and wherein said two or more of the chemical elements are present in a proper subset of the compounds.

17. The method according to claim 1, wherein the isotopic patterns of compounds used for training the supervised element classifier are theoretically derived.

18. The method according to claim 1, wherein the isotopic patterns of compounds used for training the supervised element classifier are experimentally measured.

19. The method according to claim 18, wherein the isotopic patterns of compounds used for the supervised element classifier and the isotopic pattern of the analyte ions are measured on the same mass spectrometric system.

20. The method according to claim 1, wherein determination of the presence or absence of the chemical element is used for reducing or enhancing the number of chemical elements during annotating a chemical formula to the analyte.

* * * * *